US00PP27930P2

(12) United States Plant Patent
St. Hilaire

(10) Patent No.: US PP27,930 P2
(45) Date of Patent: Apr. 25, 2017

(54) BIGTOOTH MAPLE TREE NAMED 'JFS-NUMEX 3'

(50) Latin Name: *Acer grandidentatum*
Varietal Denomination: JFS-NuMex 3

(71) Applicant: Arrowhead Center, Inc., Las Cruces, NM (US)

(72) Inventor: Rolston St. Hilaire, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 83 days.

(21) Appl. No.: 14/544,904

(22) Filed: Mar. 5, 2015

Related U.S. Application Data

(63) Continuation of application No. 14/587,882, filed on Dec. 31, 2014, now abandoned.

(51) Int. Cl.
*A01H 5/00* (2006.01)

(52) U.S. Cl.
USPC ..... Plt./224

(58) Field of Classification Search
USPC ..... Plt./224
See application file for complete search history.

(56) References Cited

PUBLICATIONS

Richards, et al., "Propagating Bigtooth Maple", Horticulture, http:/ www.Horticulture/Trees/2011-03pr, May 2011.

*Primary Examiner* — Susan McCormick Ewoldt
(74) *Attorney, Agent, or Firm* — Isaac Estrada; Deborah A. Peacock; Peacock Myers, P.C.

(57) ABSTRACT

A new and distinct cultivar of Bigtooth Maple tree named 'JFS-NuMex 3', characterized by resiliency to drought and improved resistance to fungal diseases, faster growing, branching with more upright angles, and with brighter fall colors than all other Bigtooth selections.

6 Drawing Sheets

Botanical designation: *Acer grandidentatum* 'JFS-NuMex 3'.

Cultivar denomination: 'JFS-NuMex 3'.

BACKGROUND OF THE INVENTION

The present invention relates to a new and distinct cultivar of Bigtooth Maple tree, botanically known as *Acer grandidentatum* 'JFS-NuMex 3', and commonly known as 'JFS-NuMex 3' Bigtooth Maple.

The new Bigtooth Maple (*Acer grandidentatum* 'JFS-NuMex 3') has unique foliar and growth traits. The plant shows resiliency to drought and improved resistance to tar spot fungi (*Rhytisma* spp.) and powdery mildew (*Phyllactina marissalii*), which are common fungal diseases of *Acer grandidentatum*. The new Bigtooth Maple is also faster growing, more upright and well branched than all other *Acer grandidentatum* selections, and displays brighter fall colors.

BRIEF SUMMARY OF THE INVENTION

The following traits have been repeatedly observed and are determined to be the unique characteristics of 'JFS-NuMex 3'. These characteristics in combination distinguish 'JFS-NuMex 3' as a new and distinct Maple tree:

1. Resiliency to drought;
2. Resistance to tar spot fungi (*Rhytisma* spp.) and powdery mildew (*Phyllactina marissalii*);
3. Faster growing;
4. Branches with upright angles; and
5. Brighter fall colors.

Trees of the new Bigtooth Maple 'JFS-NuMex 3' can be compared to sugar maple (*Acer saccharum*), or the established cultivar *Acer grandidentatum* 'Schmidt' (marketed as Rocky Mountain Glow® maple) (not patented). The 'JFS-NuMex 3' differ in branching angles, brighter fall colors, and faster growth.

BRIEF DESCRIPTION OF THE SEVERAL VIEWS OF THE PHOTOGRAPHS

The accompanying colored photographs, which are incorporated into and form a part of the specification, illustrate the overall appearance of the new Bigtooth Maple tree showing the colors as true as it is reasonably possible to obtain in colored reproductions of this type. Colors in the photographs may differ slightly from the color values cited in the detailed botanical description which accurately describe the colors of the new Bigtooth Maple tree.

DETAILED BOTANICAL DESCRIPTION

The aforementioned colored photographs and following observations, measurements and values describe plants grown in greenhouse and field evaluations in Las Cruces, and Boring, Oreg. The new Bigtooth Maple (*Acer grandidentatum* 'JFS-NuMex 3') had unique foliar and growth traits. The plant showed resiliency to drought as assessed through standard drought physiological testing. In nine years of field testing in Boring, Oreg., the plant performed well. During testing, *Acer grandidentatum* 'JFS-NuMex 3' was compared with two other clones of the Texas origin of the species, numerous typical seedlings of the species, numerous clones of a Utah origin, typical seedlings and established cultivars of the closely related taxa, sugar maple (*Acer saccharum*), and the established cultivar *Acer grandidentatum* 'Schmidt' (marketed as Rocky Mountain Glow® maple).

Figure 1A:
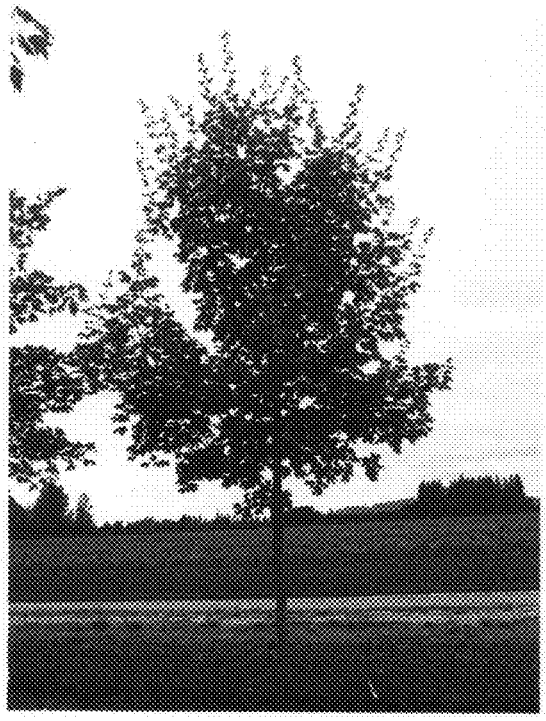
FIG. 1A is a side view photograph of an 8-year-old 'JFS-NuMex 3' tree.
Figure 1B:
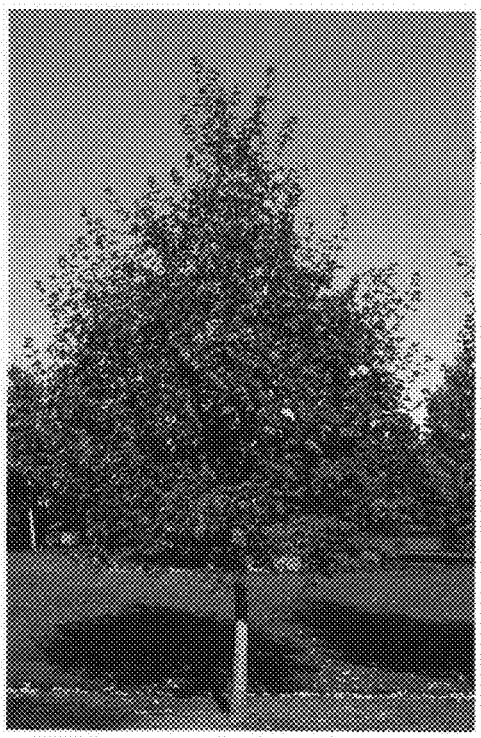
FIG. 1B is a side view photograph of a Rocky Mountain Glow® tree.

Referring to FIG. 1A, a 'JFS-NuMex 3' eight-year-old tree is shown compared to a Rocky Mountain Glow® tree in FIG. 1B. The two trees differ in form. These photographs were taken in Boring, Oreg. in the summer 2013.

Figure 2:
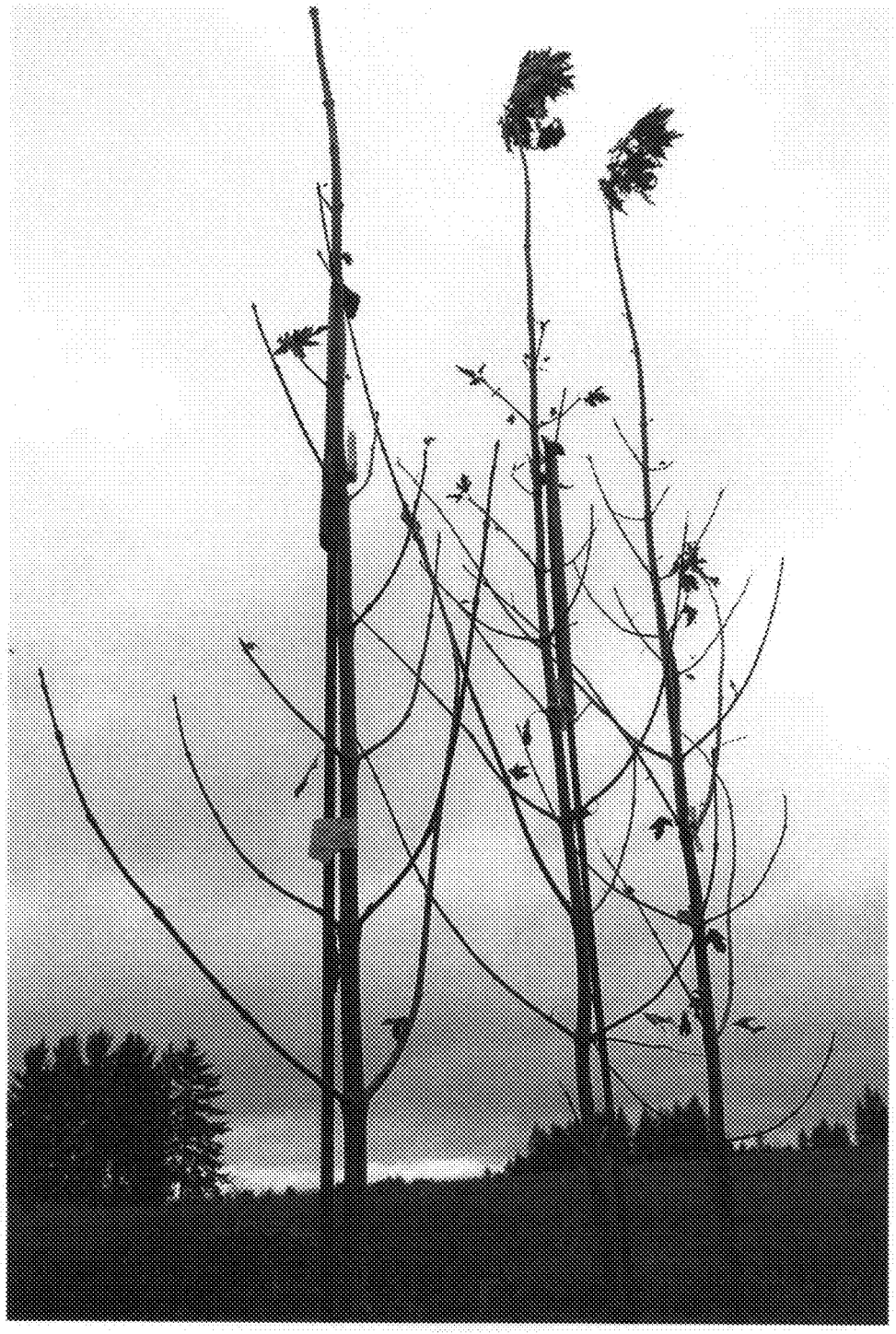
FIG. 2 is a photograph showing the branch structure on a 1-year-old 'JFS-NuMex 3' whip.
Figure 3:
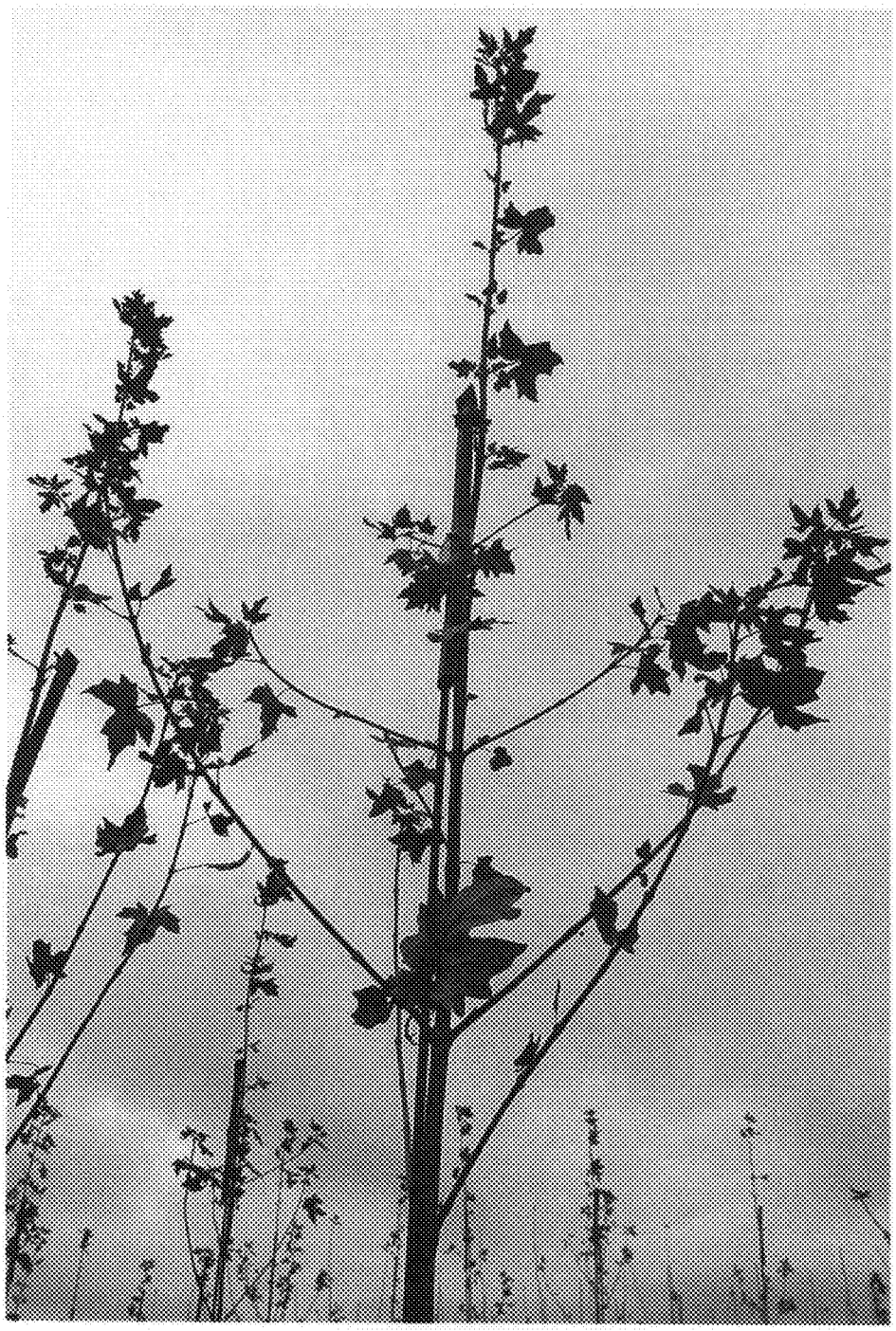
FIG. 3 is a photograph showing the branch structure of a 1-year-old Rocky Mountain Glow® whip.

Furthermore, the branch structure on a 1-year-old 'JFS-NuMex 3' whip (FIG. 2) differs from that of a 1-year-old Rocky Mountain Glow® whip (FIG. 3). The photographs in FIGS. 2 and 3 were taken in Boring, Oreg. on Nov. 25, 2014.

Figure 4:
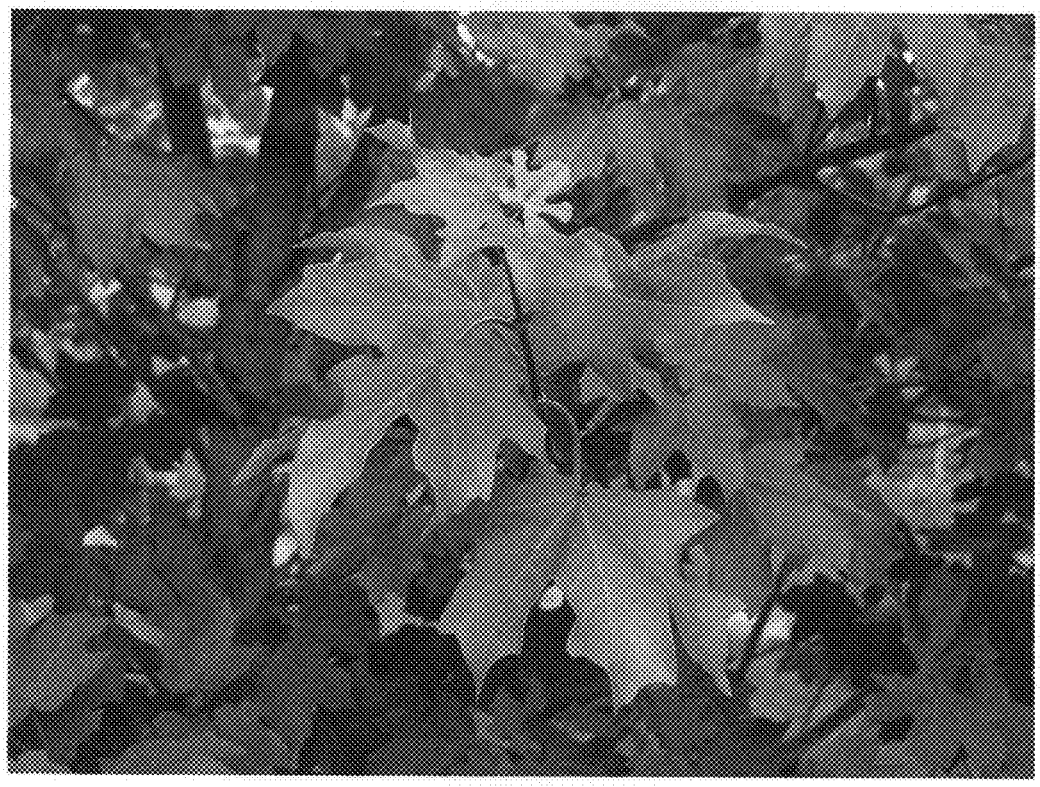
FIG. 4 is a photograph showing the summer foliage of the 'JFS-NuMex 3' tree.
Figures 5A, 5B:
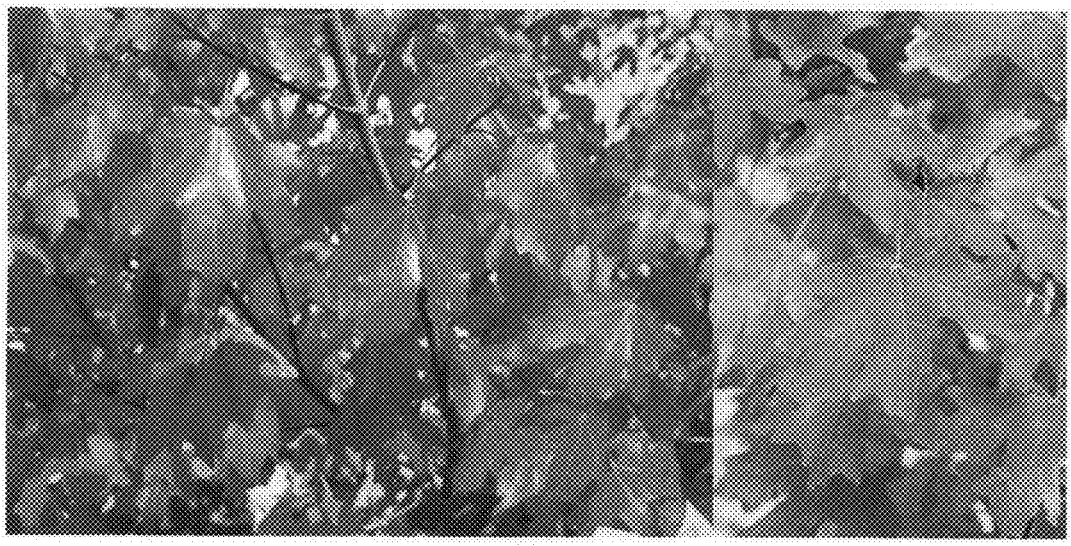
FIG. 5A is a photograph showing the fall foliage of the 'JFS-NuMex 3' tree.
FIG. 5B is a photograph showing the fall foliage of the Rocky Mountain Glow® tree.

FIG. 4 shows the summer foliage of 'JFS-NuMex 3'. The photograph was taken in Boring, Oreg. on Jul. 5, 2013. 'JFS-NuMex 3' fall color varied from yellow orange to red and had the brightest fall color observed in all *Acer grandidentatum* selections. FIG. 5A shows the fall foliage color of 'JFS-NuMex 3' while FIG. 5B shows the fall foliage of Rocky Mountain Glow®. The photograph of 'JFS-NuMex 3' was taken on Nov. 4, 2014 and the photograph of the Rocky Mountain Glow® was taken in the fall of 2013.

Figure 6:
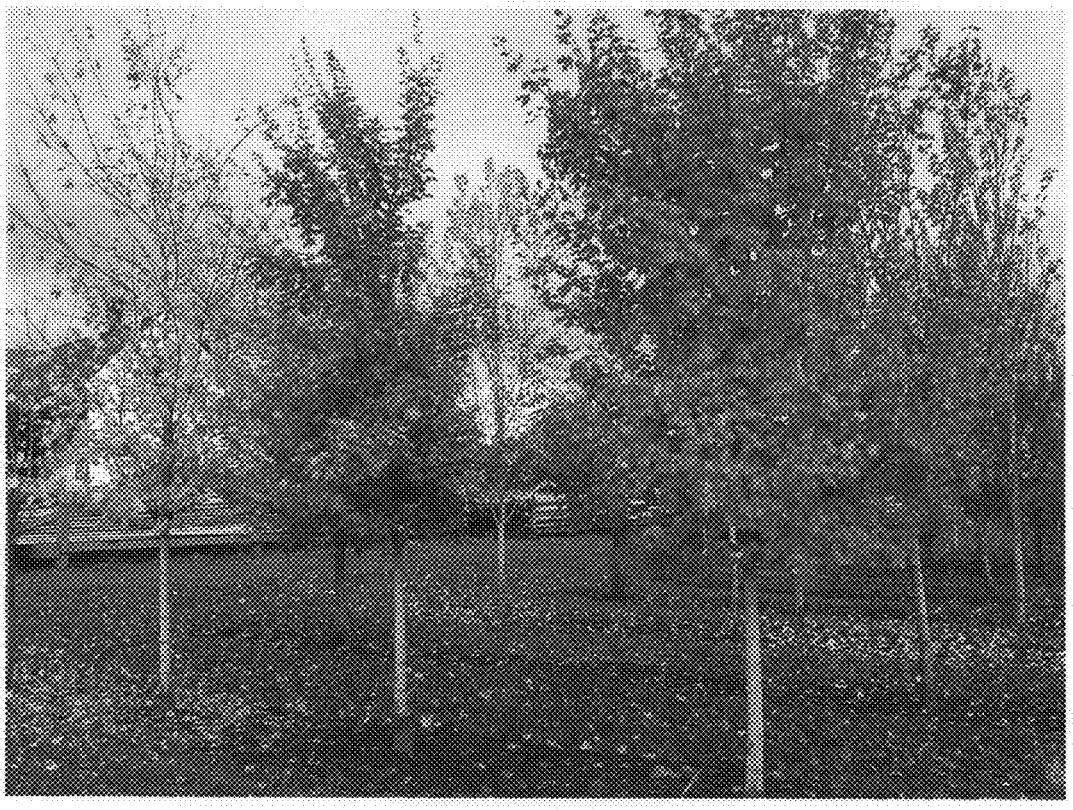
FIG. 6 is a photograph showing a comparison of the fall foliage color and form of 'JFS-NuMex 3' (right) and the NMSU 1 selection (middle), and NMSU 2 (left) selections.

Referring to FIG. 6, when compared with two Texas clones (NMSU 1 selection (middle), and NMSU 2 selection (left)), in a planting block in Boring, Oreg., 'JFS-NuMex 3' had the best nursery growth and branch structure. Another advantage of 'JFS-NuMex 3' over all other *Acer grandidentatum* selections is that it was faster growing, more upright and well branched. Furthermore, 'JFS-NuMex 3' had improved resistance to tar spot fungi (*Rhytisma* spp.) and powdery mildew (*Phyllactina marissalii*) which are common fungal diseases of *Acer grandidentatum*.

Drought tolerance testing involved initial assessment of leaf chlorophyll fluorescence, plant water relations, leaf relative water content, specific leaf weight, total leaf area, specific stem length, leaf thickness, plant height, xylem diameter, leaf, stem, and root dry weight, relative growth rate (RGR), and net assimilation rate (NAR) of plants exposed to multiple cycles of drought. A second round of drought tolerance testing involved assessment of plant water relations, relative water content, specific leaf weight, foliar stable carbon isotope composition and carbon and nitrogen content, plant height, xylem diameter, total leaf surface area, RGR, NAR, and leaf, stem, and root dry weight.

For radiation tolerance screening, the acclimation of the plant to light and shade was assessed via the assessment of the photoprotective mechanisms of the violaxanthin and lutein cycles.

Aesthetic qualities assessed included leaf morphology, leaf color, fall foliage color, foliage characteristics (tip burn and leaf tatter), pest and disease incidence, branching habits, and plant height. Foliage also was screened for leaf tip burn and leaf tatter.

Botanical designation: *Acer grandidentatum* 'JFS-NuMex 3'.

Cultivar denomination: 'JFS-NuMex 3'.

Parentage: The new Bigtooth Maple tree originated from progeny selection of half-siblings that originated from an unknown, open pollinated single-tree with unknown parentage in Vanderpool, Tex., USA. Progeny were screened for drought and radiation tolerance, and aesthetic qualities. 'JFS-NuMex 3' leaves show little to no evidence of leaf tatter. In contrast, leaves of the parent showed some evidence of leaf tatter. New foliage growth of 'JFS-NuMex 3' is distinctly greyed-orange (RHS 176A). This new foliage distinguishes 'JFS-NuMex 3' from its potential parent and many other bigtooth maple taxa. The petioles of 'JFS-NuMex 3' are red (RHS 46A). Typical petiole color for other bigtooth maples is green. The potential parent plant had a spreading rounded crown which differs from the upright oval canopy of 'JFS-NuMex 3'. This indicates that 'JFS-NuMex 3' branches more upright than its parent.

Propagation: Mature samaras (seeds) of bigtooth maples were collected from the unknown parent tree in a natural stand and with unknown parentage. After 18 weeks of cold, moist stratification, seeds were sown in a mixture of peat moss and perlite (1:1, by volume) in bench-top trays in a greenhouse and allowed to germinate. All seedlings that had the first pair of true leaves visible were transplanted individually into 3-L plastic pots filled with the mixture of peat moss and perlite ( 1:1, by volume). Seedlings (half siblings) initially were screened for tolerance to episodic drought in a greenhouse environment. Plants that had shown initial resilience to drought were transplanted to 30-L pots filled with the mixture of peat moss and perlite (1:1, by volume) and again tested for drought tolerance. Drought testing was done in an outdoor in-ground nursery production system (pot-in-pot) established in a Chihuahuan desert environment. Desirable selections were maintained in the outdoor in-ground nursery production system. Three softwood tip cuttings 0.12-0.20 inch (3-5 mm) diameter and containing two to three nodes were selected from the desirable selection in the in-ground nursery production. Leaves (lamina and petiole) were excised, and cuttings were placed between moist paper towels and shipped overnight to a nursery in Boring, Oreg. There, the 0.12-0.20 inch (3-5 mm) thick softwood tip cuttings were veneer-grafted onto a standard commercial sugar maple stock growing in the field. From grafting, one year old trees produced 7 feet tall whips. Two-year-old grafted trees produced a 1.0 to 1.25 inch (25-32 mm) caliper tree; three-year-old trees produced a 1.5 to 1.75 inch (38-44 mm) caliper tree. The ornamental traits remained stable after eight years of successive asexual reproduction. A low level of graft incompatibility between the sugar maples stock and bigtooth maple scion was observed in test plots. Overall incompatibility rates were around 5% and when incompatibility occurred, it was early in the life of the tree so incompatible trees can be culled in the nursery.

Plant description:

*Size*.—Medium-sized tree, reaching 13 feet (4.0 m) in 10 seasons, 3.2 inch (8.1 cm) caliper, when grown on its own root. Trees are typically grafted onto a standard compatible sugar maple rootstock in a commercial production system. The typical tree trunk diameter at breast height (4.5 feet) is eight to 9 inches (20-23 cm). Mature height and canopy spread of the plant is 28 feet and 18 feet, respectively. The coloration of the mature bark is brown (RHS N200B). Branch diameter of the largest branches average 5.75 inches (14.6 cm) and the color is brown (RHS N200B). Branch diameter of the largest branches average 5.75 inches (14.6 cm) and brown (RHS N200B).

*Growth habit and form*.—The plant has vigorous growth that is almost comparable to that of sugar maples. Branches are ascending and sturdy. The tree has an upright oval form.

*Cold hardiness*.—Plant has been shown to be cold hardy in USDA zones 5 [average annual minimum temperature (AAMT) of −15° F. (−26° C.) to −20° F. (−29° C.)] to zone 8 (AAMT of 20° F. (−7° C.) to 15° F. (−9° C.). Plants were also shown to be cold hardy in a test site in Aberdeen, Utah which is a borderline cold hardiness zone 4 [AAMT of −25° F. (−32° C.) to −30° F. (−34° C.)].

*Drought tolerance*.—The cultivar is developed for resiliency in managed landscapes that are challenged with drought and only requires regular deep watering post establishment.

*Heat tolerance*.—The cultivar thrives in the typical Chihuahuan desert environment of Las Cruces, N.M. And this environment is in the American Horticultural Society Heat Zone 9 [an average of 120 to 150 days per year with temperature above 86° F. (30° C.)]. The plant tolerates exposure to sun and part shade.

Foliar traits:

*Size*.—Average length (apex to petiole), 4.25 inch (108 mm); average width: 2.87 inch (73 mm). Mature leaves have five lobes with well-developed lobes that are characteristic of the Bigtooth Maples taxa.

*Type*.—Simple.

*Shape*.—Mature leaves have five well-developed palmate lobes and two smaller proximal lobes (closest to petiole) each with acuminate tips. Sinuses are rounded. Average depth of sinus between distal and middle lobes is 0.90 inch (23 mm).

*Arrangement*.—Opposite.

*Apex*.—Acuminate.

*Color*.—In summer, the adaxial surface of mature leaves are glossy and have a dark green color that corresponds to 137B on The Royal Horticultural Society (R.H.S.) Color Chart. On mature, fully expanded leaves, spring foliage color on the adaxial (upper) leaf surface is a glossy green (RHS 137B) and spring foliage color on the abaxial (lower) leaf surface is light green (RHS 138B). Leaf veins on the mature leaves are yellow green (RHS 153 B). The newly emerging spring are greyed-orange (RHS 175A) on the adaxial leaf surface and greyed-orange on the abaxial (RHS 177A) leaf surface. The twigs on the stems on the plant's current season growth are greyed-orange (RHS 176A). Fall foliage color varies from yellow orange (RHS 16A) through orange red (RHS N34C) to deep red (RHS 46C) and is the reddest bigtooth maple selection that has been observed in the test plots in Boring, Oreg.

*Petiole*.—On mature, fully expanded leaves, petiole length and diameter average 1.0 inch (2.5 cm) and 0.07 inch (1.75 mm). Petioles on mature leaves are red (46A on The R.H.S. Color Chart).

*Base*.—Acute.

*Abaxial surface*.—Pubescent with thick, unicellular trichomes. Trichomes are prominent along veins.

*Adaxial surface*.—Glabrous.

*Venation*.—Palmate with one primary prominent vein per lobe.

Fruit:

*Type*.—Double samara, samara angle of 44°.

*Size*.—0.78 inch (20 mm) long, 1.0 inch (2.5 cm) wide at membranous wing.

*Color*.—Green and turns brown at maturity. Samara matures in mid to late September in Las Cruces, N.M. Seed color varies from green (RHS 141C) when immature to brown (RHS 200C) when mature.

What is claimed is:

1. A new and distinct Bigtooth Maple tree named 'JFS-NuMex 3' as illustrated and described.

* * * * *